United States Patent [19]
Bullister

[11] Patent Number: 5,865,827
[45] Date of Patent: Feb. 2, 1999

[54] VACUUM DEVICE FOR SECURING HUMAN TISSUE

[76] Inventor: Edward T Bullister, 86 Concord St., Newton, Mass. 02162

[21] Appl. No.: 868,648

[22] Filed: Jun. 3, 1997

[51] Int. Cl.$^6$ .................................................. A61B 17/00
[52] U.S. Cl. .......................... 606/1; 294/64.1; 294/64.3; 248/362
[58] Field of Search ..................... 606/1, 119, 121–123; 294/64.1, 64.3, 65; 414/627; 271/90, 99, 106, 107; 600/201, 203, 206; 604/176; 433/184–186; 29/743; 248/362, 363

[56] References Cited

U.S. PATENT DOCUMENTS

| | | | |
|---|---|---|---|
| 809,360 | 1/1906 | Dible . | |
| 2,227,673 | 1/1941 | Price . | |
| 2,702,038 | 2/1955 | Uddenberg . | |
| 3,794,044 | 2/1974 | Vennard | 128/352 |
| 4,486,013 | 12/1984 | Vander Syde | 271/107 |
| 4,558,755 | 12/1985 | Lundin | 177/147 |
| 4,597,391 | 7/1986 | Janko | 128/361 |
| 4,730,617 | 3/1988 | King | 128/352 |
| 4,917,427 | 4/1990 | Scaglia | 294/64.1 |
| 4,961,606 | 10/1990 | Nilsson | 294/65 |
| 5,019,086 | 5/1991 | Neward | 606/123 |
| 5,033,730 | 7/1991 | Davies | 271/106 |
| 5,192,070 | 3/1993 | Nagai | 271/90 |
| 5,193,796 | 3/1993 | Nagai | 271/90 |
| 5,196,003 | 3/1993 | Bilweis | 606/1 |
| 5,213,385 | 5/1993 | Nagai | 294/64.1 |
| 5,224,947 | 7/1993 | Cooper | 606/123 |
| 5,344,202 | 9/1994 | Ramler | 294/64.1 |
| 5,395,379 | 3/1995 | Deutchman | 606/123 |
| 5,415,160 | 5/1995 | Ortiz | 128/20 |
| 5,507,752 | 4/1996 | Elliot | 606/123 |

Primary Examiner—Michael Peffley
Assistant Examiner—Bryan K. Yarnell

[57] ABSTRACT

A vacuum device (10) has a collapsible cover (18) capable of maintaining a seal with a flexible surface (64) such as human tissue. A set of shaping members (20) support the cover (18) against collapse into the evacuated region in the interior, yet readily flex to maintain the seal with the deforming tissue without the need for an excessive sealing force.

17 Claims, 4 Drawing Sheets

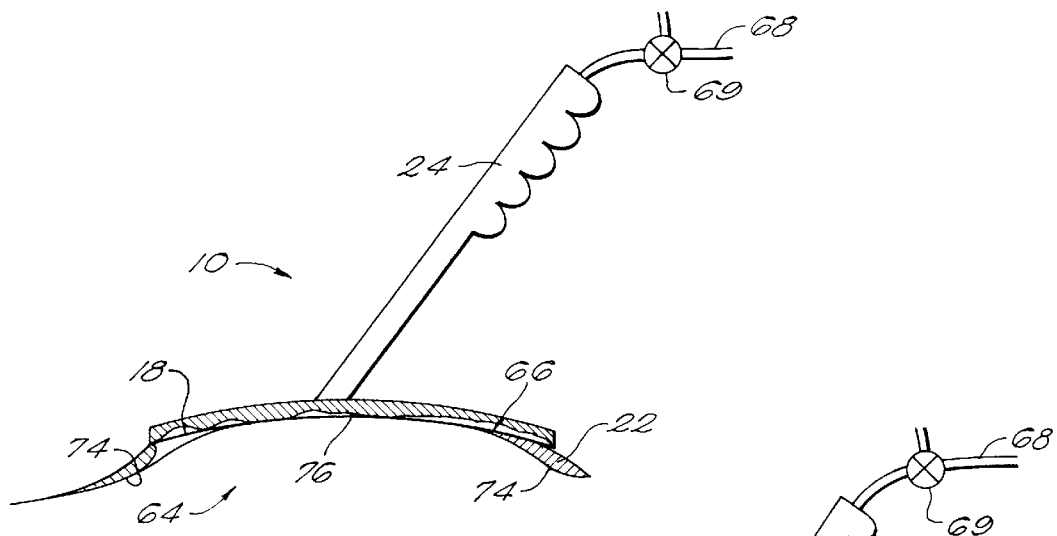
FIG. 8A
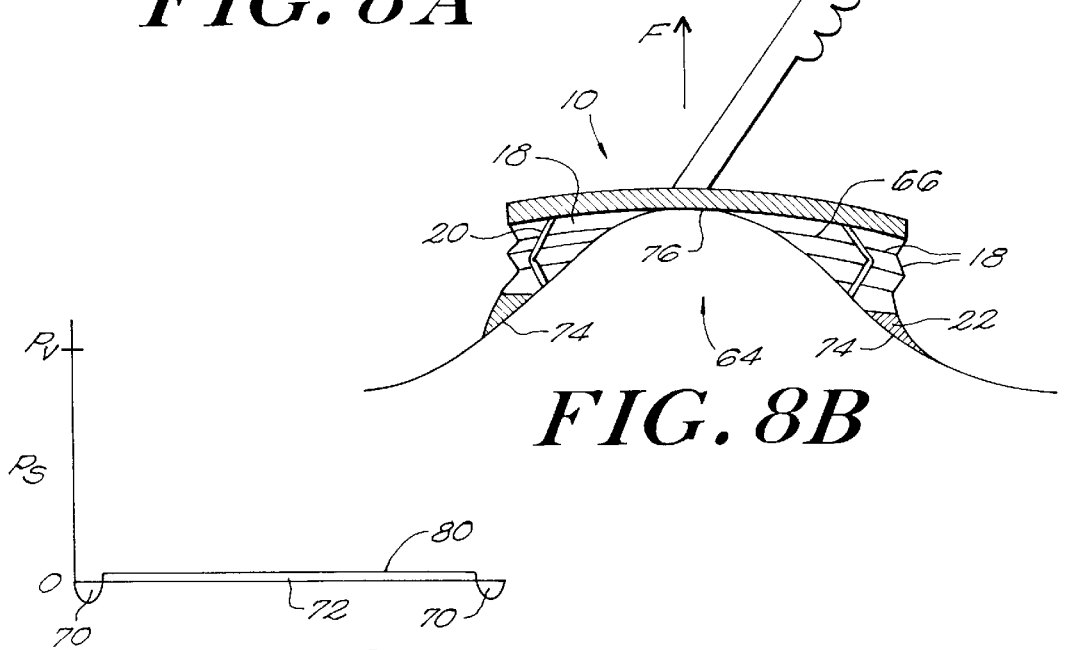
FIG. 8B
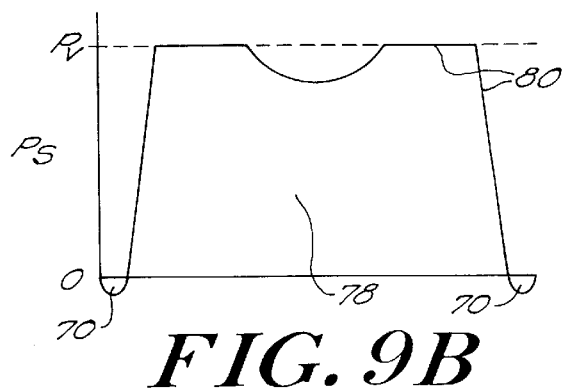
FIG. 9A
FIG. 9B

VACUUM DEVICE FOR SECURING HUMAN TISSUE

FIELD OF INVENTION

This invention relates to devices for manipulating flexible surfaces and specifically to surgical devices in which vacuum is used to position and manipulate human tissue.

BACKGROUND

Various surgical procedures require that a region of tissue be positioned and manipulated. Two types of devices for holding and manipulating objects are clamps and vacuum devices.

Clamps and forceps apply opposing forces from two directions. However, access to two sides (e.g., front and back) of a piece of tissue is not always available. When only one side of the tissue is available, a portion of the tissue must be "pinched" between the jaws of the clamp. This can be traumatic to the tissue.

Clamps can easily apply excessive forces to local areas. For example, in vascular surgery, excessive clamping force can collapse a blood vessel. In such a collapse, the tubular vessel is flattened, stopping the flow of blood and potentially damaging the vessel tissue.

Vacuum devices present an alternative to clamps and forceps. The vacuum device is held adjacent to a surface to create an enclosed volume. Vacuum may be drawn in the enclosed volume through a port. The enclosed volume is otherwise sealed from its surroundings. Forces and displacements applied to the vacuum device are communicated to the surface via the suction pressures.

However, standard vacuum cups designed for use on rigid surfaces do not work as well on surfaces of flexible materials such as human tissues. When force is applied to soft tissue, the tissue deforms. In some casesm the deformation is linear and elastic and easily quantified. More often with biological tissues, the deformation is highly nonlinear, and may include a time-dependent, visco-elastic component. For example, human tissue exhibits both elastic and visco-elastic properties. As a result the deformation of human tissue depends on both the force currently applied and also on the cumulative past history of forces applied to the tissue. When forces are applied to human tissue for extended periods, the tissue typically undergoes large deformations and the seal with a standard vacuum cup can be easily lost.

To avoid losing the seal with flexible human tissues, a deeped vacuum cup has been developed and is currently used for childbirth extraction. For example, in U.S. Pat. No. 5281229 Neward discloses an obstetrical vacuum extractor cup. In cups such as these, the deep walls of the cup enable a seal to maintained even with highly deformed tissue. The cup is axisymmetric; the deep walls have a circular cross section prevent buckling and collapse of the cup when a vacuum is drawn.

While such a vacuum is drawn within these deepened cups, the cups can impose large forces and/or deformations to the tissue. These forces to the tissue can be significant even when no overall net force is applied to the cup.

For example, when no force is applied to the handle of a deepened cup, calculation of a force balance shows that no net force is applied from the cup to the tissue. (In this calculation, the small weight of the cup is neglected). To achieve the zero net force on the tissue, the pulling force on the tissue caused by the vacuum in the interior of the cup is balanced by an equal pushing force applied to the tissue by the rim of the cup. These forces which act on the tissue when no net external force is applied to the vacuum device are defined herein as residual forces.

The residual forces can cause undesirable deformations and possible trauma to the tissue. Obstetrical cups create a large deformation called an "artificial caput succedaneum" on a portion of the fetal head. This condition requires a considerably long period for a complete cure and sometimes leaves a permanent scar on the head of the fetus. Additionally, the gross distortion of the infant scalp causes bruising. This bruising elevates the blood levels of bilirubin, which the immature infant liver is not yet capable of removing, and jaundice can result.

Furthermore, the effectiveness of the vacuum device diminishes after the shape of the tissue conforms to the shape of the rigid cup. After the tissue has deformed to the cup shape, any additional deformation can result in loss of the seal between the cup and the tissue.

An alternative to deepened cups are cups of a very small diameter. With smaller diameter cups, the applied forces are much smaller. Furthermore, the elastic and viscoelastic effects are mitigated by the small length scales. Small length scales mean that the tissue must be deformed to a smaller radius of curvature to separate from the cup. Correspondingly higher stresses are encountered; the materials appear effectively stiffer as the length scales decrease. However, the small forces that these small cups can deliver severely limit their usefulness for securely holding tissue.

Therefore, there is a need for a system for holding tissue during surgery which can be easily applied from one side of the tissue, which can securely hold the tissue without excessive deformation or damage, and in which the residual forces are very small.

OBJECTS AND ADVANTAGES

It is an object of this invention to secure tissue during operation such that:

a) soft tissue can be securely held, b) tissue can be securely held when only the front surface of the tissue is accessible, c) the tissue surface be held in a predetermined shape, d) tractions are distributed over the surface of the tissue, e) the tissue held beneath the securing device is visible, f) imminent separation of the device from the tissue is detectable and can be avoided, g) the device can secure noncircular areas of tissue, h) the device can secure blood vessels without pinching, i) the device can maintain its grip on a tissue surface undergoing large deformations, and j) residual forces applied to the tissue are minimized.

SUMMARY

A vacuum device enables flexible surfaces to be secured and manipulated. In particular, the device can secure surfaces of human tissue with minimum trauma and without applying unnecessary forces to the tissue.

The device enables an object to be secured by only accessing the front surface of the object. The forces used to secure the object are spread over a wide area, without the dangers associated with large localized forces. The device can secure noncircular and nonplanar areas of tissue.

A structural foundation of the device supports shaping members. These shaping members support a flexible cover impermeable to fluid. The structural foundation has a contour surface shaped to conform to the desired shape of a flexible surface.

When the vacuum device is held against the flexible surface, the combination of the contour surface, cover, seal, and flexible surface bound an enclosed volume. Forces applied to the foundation are communicated to the flexible surface through suctions in the enclosed volume. The cover and seal flex to maintain contact with the flexible surface while it is being manipulated by the vacuum device.

BRIEF DESCRIPTION OF THE DRAWING

FIG. 8A shows the operation of the vacuum device without net forces applied.

FIG. 8B shows the operation of the vacuum device with net forces applied.

FIG. 9A plots the surface pressures applied to the tissue at a cross section without net forces applied.

FIG. 9B plots the surface pressures applied to the tissue at a cross section with net forces applied.

Figure 1:
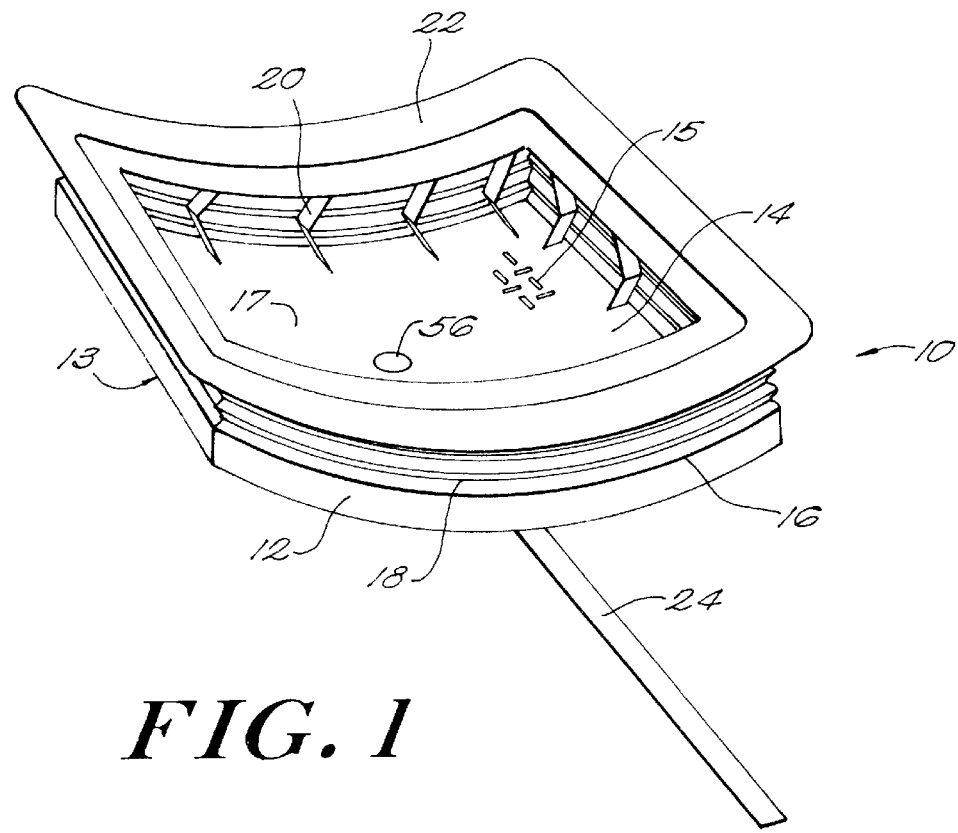
FIG. 1 shows a perspective view of an embodiment of the vacuum device.

REFERENCES NUMERALS IN DRAWINGS 10 vacuum device
12 foundation
13 external surface
14 contour surface
15 ridges
16 perimeter
17 interior area
18 cover
20 shaping members
22 seal
24 handle
26 tangent vector
28 normal vector
30 transverse vector
32 attachment point
34 hinge member
36 first arm
38 second arm
40 hinge member
42 distal end
43 piston
44 axial journal bearing
46 spring
52 proximal edge
54 distal edge
56 port
58 distal hinge member
60 acute angle
61 parallel edge
62 parallel edge
63 flange
64 flexible surface
66 vacuum cavity
68 vacuum source
69 valve
70 sealing force
72 residual force
74 sealing surface
76 suction surface
78 pulling force
80 suction pressure

DESCRIPTION OF THE INVENTION

Referring to FIG. 1, a vacuum device 10 has a foundation 12 with an external surface 13 and a contour surface 14. The contour surface may have small ridges 15. Along the edge of the contour surface 14 is a perimeter 16. On the contour surface 14, inside the the perimeter 16 is an interior area 17. A cover 18 is attached to the foundation 12 near the perimeter 16. A set of shaping members 20 are attached to the foundation 12 near the perimeter 16. A seal 22 is attached to the cover 18. A handle 24 is attached to the foundation 12. A port 56 in the foundation 12 may allow passage of a fluid. The foundation 12 may be constructed of a transparent material.

Coordinates

Figure 2:
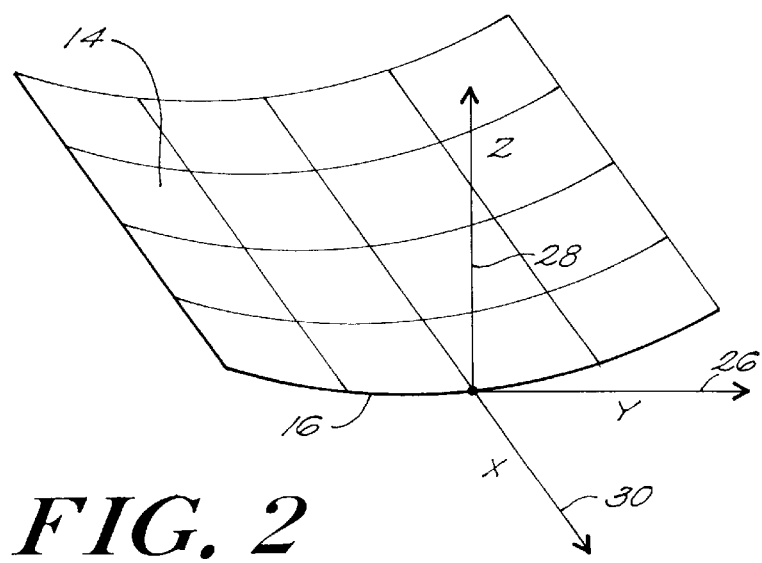
FIG. 2 details the contour surface, and establishes a coordinate system for a given point on its perimeter.

FIG. 2 shows a detailed view of the contour surface 14 and its perimeter 16. A local Cartesian coordinate system XYZ is herein defined at a given point P on the perimeter 16.

A tangent plane is the plane tangent to the contour surface at P. The XY plane in the XYZ coordinate system coincides with this tangent plane.

The tangent vector 26 is the vector tangent to the perimeter 16 at point P. The tangent vector 26 coincides with the Y axis. In the (undesirable) case of a sharp corner, the tangent vector 26 at the corner is to be taken as the average of the tangent vectors on either side of the corner.

The normal vector 28 is defined as the direction perpendicular to the tangent plane at P. The normal vector 28 coincides with the Z axis.

The transverse vector 30 is the direction parallel to the tangent plane and perpendicular to the tangent vector 26 at P. The transverse vector 30 coincides with the X axis.

The transverse vector 30, the normal vector 28, and the tangent vector 26 are mutually perpendicular and coincide with the orthogonal Cartesian XYZ coordinate system.

Herein, the term outward refers to a direction aligned with the transverse vector 30 (the positive X direction), and inward refers to the direction opposite to the transverse direction (the negative X direction).

The analysis which will follow will reference this specific XYZ coordinate system at this specific point P. Because the contour surface 14 and its perimeter 16 may be curved, a given XYZ coordinate system is valid only locally. However, a local XYZ coordinate system may be defined for any point on the perimeter 16 and this analysis may be applied to any point on the perimeter 16.

For example, the normal and transverse directions of stiffness of a given shaping member 20 are defined with respect to the the local contour surface. The local contour surface is at a point adjacent to where the end of the given shaping member 20 is attached. This analysis done for a single shaping member 20 is valid for all shaping members 20.

Shaping Members

Figure 3A:
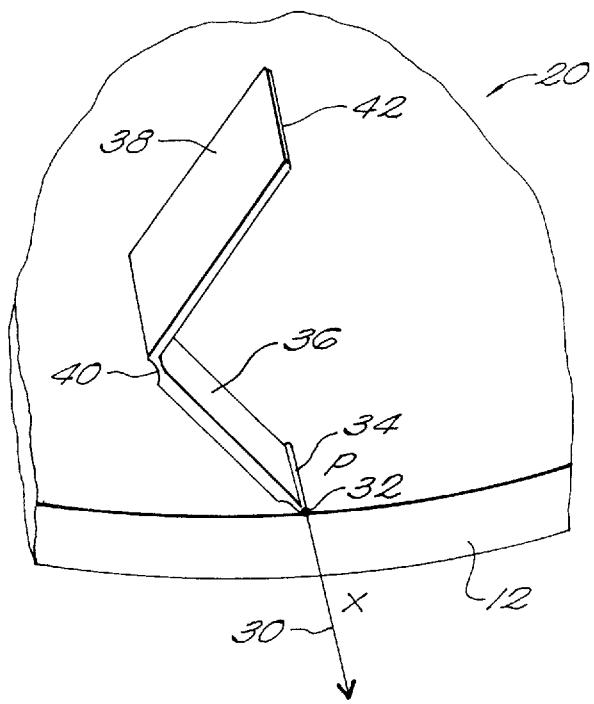
FIG. 3A details an embodiment of a shaping member for the device.

Referring to FIG. 3A, a shaping member 20 is attached to the foundation 12 at an attachment point 32 through a hinge member 34. The hinge member 34 is attached to a first arm 36. The axis of rotation of the hinge member 34 is aligned parallel to the transverse vector 30 to restrict movement of the arm 36 in the transverse direction (to restrict inward and outward movement of the arm).

A second arm 38 is attached to the end of the first arm 36 through a second hinge member 40. The axis of rotation of the second hinge member 40 is also aligned parallel to the transverse vector 30.

The hinge members 34 and 40 may have axle and journal bearing components (not shown) similar to those in a standard piano hinge. The hinge members 34 and 40 may alternately be sections of material of reduced thickness which can deform elastically or plastically. The thickness are reduced in a direction perpendicular to the transverse vector 30 with respect to a greater thickness in a direction parallel to the transverse vector 30. The elastic deformation of hinge members 34 and 40 may act as a spring acting to push the distal end 42 of the shaping member 20 away from the foundation 12.

Referring again to FIG. 3A, the shaping member 20 allows movement of points on the arms in the Y and Z directions. In particular, the distal end 42 of arm 38 can move independently in the Y and Z directions. In a simplified design, only a single arm 36 is used. However, the distal end 40 of this single arm has its movement in Y and Z directions coupled to move in a circular arc. This coupling is not always desirable.

Figure 3B:
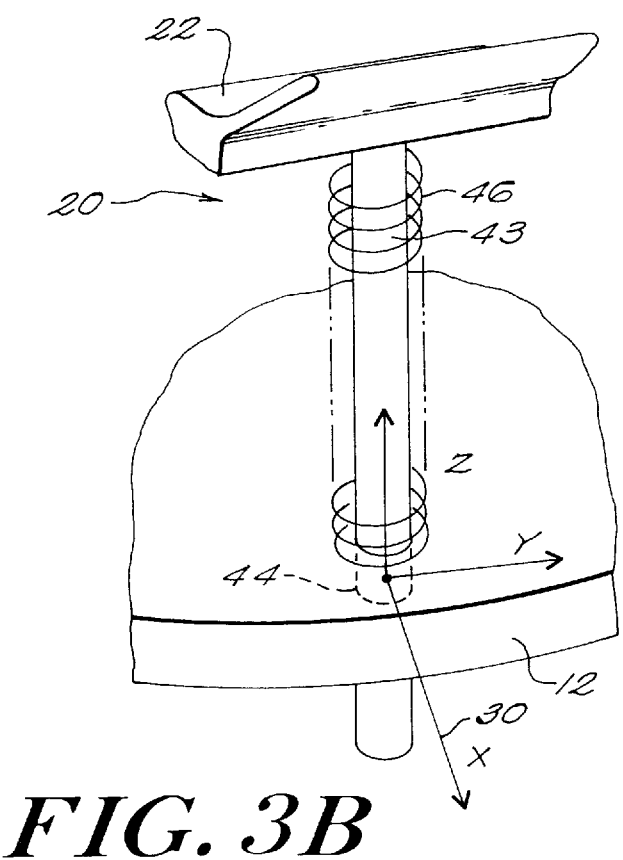
FIG. 3B details an alternate embodiment of a shaping member for the device.

Referring now to FIG. 3B, the shaping member 20 has a piston 43 which is free to slide within the axial journal bearing 44 in the foundation 12. The axes of the piston 43 and axial journal bearing 44 are aligned parallel to the normal vector 28. The end of piston 43 is attached to a seal 22. A spring 46 acts to push the seal 22 away from the foundation 12 in the direction of the normal vector 28.

The shaping member of FIG. 3B restricts the movement of piston 43 in both the X and Y directions, and allows movement in only the Z direction.

Cover

Figure 4:
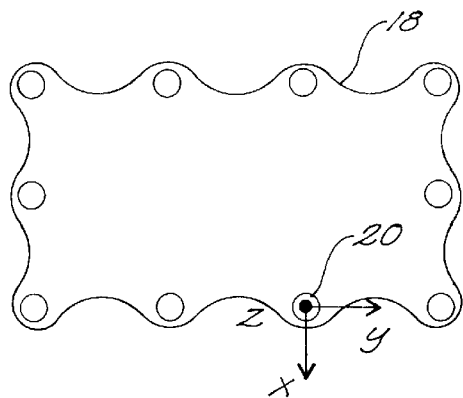
FIG. 4 shows a cover supported by a set of shaping members.

Referring to FIG. 4, a cover 18 is flexible, impenetrable to the passage of fluid, and is supported by shaping members 20 to resist inward movement.

The cover 18 is constructed as a sheet of a relatively thin material. This thin material may be easily bent and collapses under when compressive stresses are applied to one of its longer dimensions. However, the cover 18 can support tensile forces so that there are no large changes in the length of the loop under operating suctions pressures.

In this embodiment, the cover 18 forms a closed loop to the outside of (to the outward direction of) the shaping members 20. The shaping members 20 thereby physically block the inward movement of the cover 18. In other embodiments, the cover 18 may form a closed loop inside the shaping members 20 and be attached to the shaping members 20 to prevent inward movement of the cover 18.

Figure 5:
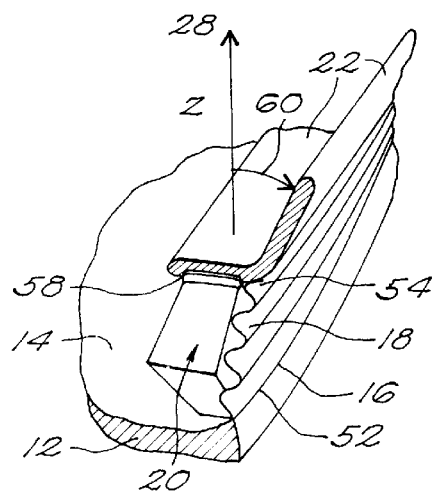
FIG. 5 shows a shaping member supporting a cover and a seal.

Referring to FIG. 5, the cover 18 has a proximal edge 52 and a distal edge 54. The proximal edge is attached to the foundation 12 such that the combination of the cover 18 and foundation 12 can form a cavity impermeable to fluid except through a port 56.

The distal edge 54 is movable in a normal direction with respect to the proximal edge 52 and with respect to the foundation 12. The distal edge 54 may flex to adapt to the contour of a flexible surface. The distal edge of the sheet may contact a flexible surface directly or through a seal 22.

The cover 18 is is sized such that its length, as measured around the closed loop, is approximately the length of the perimeter 16. As a result, the cover 18 has a relatively tight fit around the shaping members 20.

The width of cover 18 is measured by the distances along its surface between points on the proximate edge 52 and nearest points on the distal edge. The width of cover 18 is substantially greater than the maximum working distance between the foundation 12 and the seal 22. The excess cover material is seen in folds aligned parallel to the tangential vector 26. The folds are also visible in the cut view of the cover 18 in FIG. 5 and FIG. 8B.

As a result of the tight fit of the cover 18 around the shaping members 20, inward forces on the cover 18 are readily transferred to the shaping members 20. As a result of the loose fit of the cover 18 between the foundation 12 and the seal 22, inward forces on the cover 18 are not readily transferred to the seal 22 nor to the foundation 12 (see FIG. 5). The transfer of force to the seal is undesirable because it can lead to premature separation of the seal 22 from the surface with which it is in contact.

Seal

Referring again to FIG. 5, the seal 22 is attached to the cover 18 along its distal edge 54. The proximal edge 52 of cover 18 is attached to the contour surface 14 near its perimeter 16.

The seal 22 is attached to the distal edge 54 of the cover 18 such that the combination of the seal 22, cover 18, and foundation 12 can form a cavity impermeable to fluid except through the port 56.

The seal 22 is of higher structural integrity than the cover 18. The seal 22 is stiffer than cover 18 with respect to bending. The distal ends 42 of the shaping members 20 may be attached to the seal 22 through a distal hinge member 58.

An outer portion of the seal 22 may be aligned at an acute angle 60 with respect to the normal vector 28 as shown in FIG. 5.

EMBODIMENTS WITH SPECIFIC CONTOUR SURFACE SHAPES

Figure 6:
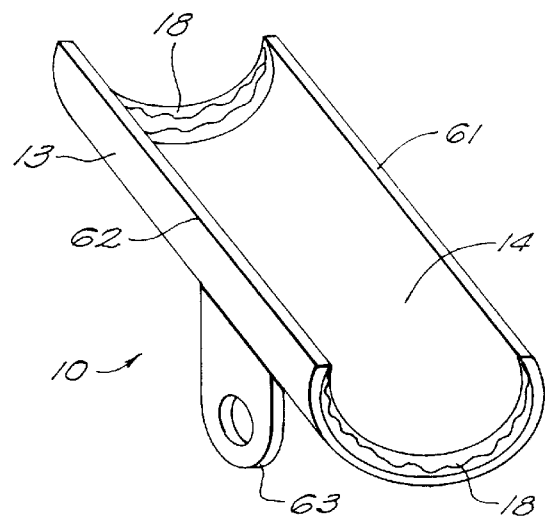
FIG. 6 shows a perspective view of an embodiment of the vacuum device designed for vascular surgery.

FIG. 6 shows an embodiment of the device for use in vascular surgery. The contour surface 14 has the shape of a semicylinder whose diameter is approximately that of a blood vessel to be secured. Parallel edges 61 and 62 are aligned with the cylinder.

The cover 18 is attached to a portion of the perimeter 16 of the contour surface 14.

The flange 63 shown in this embodiment is a means alternative to the handle 24 shown in FIG. 1 for delivering force to the foundation 12.

Figure 7:
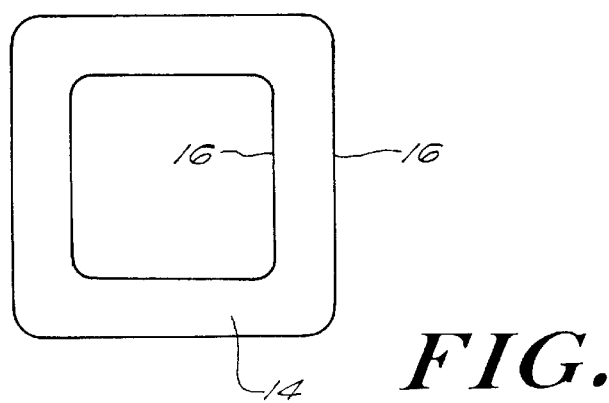
FIG. 7 shows an embodiment of the vacuum device which has an annular topology.

FIG. 7 shows an embodiment of the device in which the contour surface 14 has the topology of an annulus. In this embodiment, the contour surface 14 is bounded by two perimeters 16. This configuration leaves an area of a flexible surface 64 inside the annulus accessible by surgical or other instruments.

OPERATION

Referring to FIG. 8A, the vacuum device 10 is first held adjacent to a flexible surface 64. A vacuum cavity 66 is formed bounded by the following bounding surfaces: the contour surface 14, the cover 18, the seal 22, and the flexible surface 64.

If the device has a port 56, the port 56 is connected to a vacuum source 68. Connection with a vacuum source removes excess air from the vacuum cavity 66 and can remove air which subsequently leaks into the vacuum cavity 66. This vacuum source 68 may be a hospital vacuum supply supplied via a tube. Alternately, the vacuum may be supplied manually through a standard flexble bulb (not shown) to avoid the obtrusiveness of the tube.

Referring to FIG. 8B, a pulling force is next applied to the vacuum device 10 through the handle 24. This pulling force is transferred to the flexible surface 64. The flexible surface 64 deforms in response to the force. If the flexible surface 64 is a surface of human tissue, the tissue undergoes elastic, viscous, and visco-elastic deformation.

A valve 69 may regulate communication of fluid between the vacuum cavity 66 and vacuum source 68. The valve 69 may also allow vacuum cavity 66 to vent to the atmosphere. The valve 69 enables easy attachment and detachment of the vacuum device 10.

Forces Acting on Tissue

Referring to FIGS. 8A, 8B, 9A, and 9B, the forces acting on the tissue will be discussed.

The suction pressure Ps plotted in FIGS. 9A and 9B is defined as the negative of the gauge pressure. Where pressure is atmospheric Ps=0; in a total vacuum, Ps=760 mm Hg.

Where an vacuum source 68 has a suction pressure Pv, the maximum suction pressure applied to the tissue can be controlled by adjusting Pv. In areas where the tissue does not contact the contour surface, the suction applied to the tissue is Pv. In areas where the tissue does contact the contour surface, the suction pressure is less than or equal to Pv.

In regions in which the tissue does not contact the contour surface, only normal suction forces can be applied to the tissue. In contrast, in regions in which the tissue does contact the contour surface, both the normal (suction or pressure) and the tangential (shear) components of the traction force can be applied.

FIG. 8A shows a cross sectional cut of the device 10 an operating condition in which zero net force is applied to the device 10. A free body diagram shows that (neglecting the weight of the device 10) zero net force is therefore applied to the flexible surface 64.

As a result of the forces imparted to the seal 22 by the shaping members 20 or springs 46, a small sealing force 70 is imparted by the seal 22 to the portion of the surface 64 which the seal contacts. This area is the sealing surface 74. To maintain the zero net force on the tissue, an equal suction force is applied to the tissue inside the seal. This area is the suction surface 76. This suction force applied to the suction isurface 76 when no net force is applied to the vacuum device 10 is defined as the residual force 72.

The sealing force 70 is calculated as the surface integral of the pressure exerted by the seal integrated over the sealing surface 74. The goal is to maintain a sealing pressure at each point on the sealing surface 74 which both small and always positive. A small sealing force 70 is desirable to reduce residual force 72. A positive sealing force 70 is desirable to prevent leakage between the seal 22 and the flexible surface 64.

FIG. 8B shows a cross sectional cut of the device 10 in an operating condition in which the surgeon applies pulling force to the device 10. The distribution of this pulling force on the flexible surface 64 is shown in FIG. 9B. In this case, the total force applied by the surgeon is equal to the pulling force 78 applied to the suction surface 76, less the sealing force 70 applied to the sealing surface 74.

Inside the vacuum cavity 66, the air has a pressure equal to the suction pressure 80. The pressure exerted to the tissue is less than or equal to the suction pressure 80. Where the tissue is separated from the contour surface 14 and exposed to the air, the pressure is equal to the suction pressure 80. Where the tissue contacts the contour surface 14, the pulling pressure is less than the suction pressure 80.

This suction pressure 80 inside the vacuum cavity 66 causes the cover 18 to be sucked inward. The shaping members 20 support the cover 18 against this inward movement and collapse.

The inward collapse can limit the maximum force which can be applied by the vacuum device 10. The resistance to this collapse depends on the stiffness of the shaping members 20 to transverse forces.

The minimum residual force which is applied is limited by stiffness of the shaping members 20 to normal forces.

A good device has a high ratio of maximum force to residual force. This corresponds to shaping members 20 having a high ratio of transverse stiffness to normal stiffness. This ratio in the instant invention can be at least 5:1.

Seal

Referring to FIGS. 8A and 8B, the shaping members 20 allow the seal 22 to move with the deforming flexible surface 64 to maintain contact and prevent leakage into the vacuum cavity 66. It is critical that the seal 22 be sufficiently flexible for this movement in the direction parallel to the normal vector 28. The seal 22 should be less flexible to movements in a direction perpendicular to normal vector 28.

The seal 22 may be directly supported through attachment to the distal ends 42 of the shaping members 20 as shown in FIG. 5.

The seal 22 may be cast with the nominal shape of the tissue surface to which it is to mate, so that bending from this nominal shape is minimized.

Shear Tractions

The contour surface 14 conform to the desired shape of the tissue to on which it is placed.

In FIG. 1, the ridges 15 on the contour surface 14 can increase the amount of shear which may be applied from the foundation 12 to the flexible surface 64 without slippage.

Separation

The foundation 12 may be made of a transparent material. This enables the surgeon to see the tissue being held. It is also makes it possible to visually detect separation between the contour surface 14 and the flexible surface 64. Generally, an air gap is associated with such a separation. This air has a refractive index significantly lower than liquid bodily fluids which would otherwise lie between the contour surface 14 and the tissue having the the flexible surface 64. This gives a distinctly different appearance to the separated regions.

This visual que enables the surgeon to monitor the amount of the contour surface 14 separated. When an excessive amount of area is separated, it is an indication of imminent separation of the seal 22 from the sealing surface 74. Once the seal 22 separation process begins, it proceeds very rapidly. The result is the separation of the entire vacuum device 10.

Vascular Surgery

FIG. 6 shows an embodiment of the device for use in vascular surgery. In this application, blood vessels have a tubular, cylindrical shape, and the contour surface 14 has the shape of a portion of a cylinder. Herein, the term "cylinder" refers a circular cylinder which corresponds to the shape of walls of a tube, but does not include the circular areas which correspond to the ends of the tube.

The embodiment of FIG. 6 illustrates an important example in which the seal 22 in not required to extend around the entire perimeter 16 of the contour surface 14.

The cross section of the contour surface 14 may be a circular arc greater then 180 degrees. This cross section takes the shape of the letter "C". In this configuration, parallel edges 61 and 62 are spaced a distance less than one cylinder diameter, so that forces pulling the blood vessel out of the cylinder tend to push the blood vessel through a more narrow passage and thereby increase the sealing force. This obviates the need for a seal 22 along this portion of the perimeter 16. In this configuration, seals 22 are needed only near the ends of the cylindrical contour surface 14.

Operation Summary

Thus, in contrast to prior art, the device can apply large suction forces to a flexible surface when a pulling force is applied, and apply only minimum residual forces when the pulling force is not applied.

This operational capability is facilitated by shaping members 20 which support a flexible cover 18 and seal 22. This support is not isotropic; it has a very high ratio of stiffness in a transverse direction vs. stiffness in the normal direction. These shaping members 20 can be configured almost arbitrarily while maintaining this high stiffness ratio.

These structures allow embodiments of the device to be configured in nearly arbitrary shapes so that a wide variety of flexible surfaces may be held in surgical and other applications.

Conclusions, Ramifications, and Scope

Thus the reader will see that the vacuum device 10 of the invention provides a secure, controlled, and highly versatile means of connecting to a flexible surface.

While the above contains many specificities, the specific details of the preceeding description merely illustrate some of the preferred embodiments of this invention and should not be construed as limiting the scope of the invention. For example, other shapes of the contour surface allow attachment to other surface shapes. Accordingly, the scope of the invention should be determined not by the embodiments illustrated, but by the appended claims and their legal equivalents.

I claim:

1. A device for securing flexible surfaces, comprising:
  a) a foundation having:
    i) an external surface; and
    ii) a contour surface having an interior area and an outer perimeter;
  b) a plurality of shaping members spaced around said outer perimeter, each shaping member having a first end connected to said foundation at said perimeter and a second end; said shaping member having a first stiffness with respect to translation of said second end relative to said foundation normal to said contour surface and a second stiffness with respect to any translations of said second end relative to said foundation transverse to said outer perimeter, said second stiffness being greater than said first stiffness; and
  c) a fluid impermeable cover connected to said foundation such that an interior volume is bounded by said contour surface of said foundation and said cover, said cover being supported by said shaping members to resist transverse movement toward said interior volume.

2. The device of claim 1, further comprising a port for flow of fluid between said interior volume and an external volume.

3. The device of claim 1, further comprising a handle connected to said foundation.

4. The device of claim 1, further comprising an attachment lug connected to said foundation such that forces may be imparted to said foundation through said attachment lug.

5. The device of claim 1, wherein said flexible surfaces are surfaces of human tissue.

6. The device of claim 1, wherein said outer perimeter is of noncircular shape.

7. The device of claim 1, further comprising a seal, wherein:
  a) said seal is configured as a closed loop;
  b) said cover has a distal edge configured as a closed loop;
  c) said seal is attached to said cover along entire said distal edge such that the combination of said seal and said cover are impermeable to fluid.

8. The vacuum device of claim 1, wherein each of said shaping members comprises a first arm.

9. The vacuum device of claim 8, wherein each of said shaping members further comprises a first hinge member attaching said first arm to said foundation, said first hinge member having an axis of rotation substantially transverse to said perimeter.

10. The vacuum device of claim 9, wherein each of said shaping members further comprises:
  a) a second arm; and
  b) a second hinge member;
    said second hinge member connecting said second arm to said first arm,
    said second hinge member having an axis of rotation substantially transverse to said perimeter.

11. The vacuum device of claim 1, wherein said second stiffness is at least 5 times greater than said first stiffness.

12. The vacuum device of claim 1, wherein said foundation is made of a transparent material.

13. The vacuum device of claim 1, wherein said contour surface has substantially the shape of a portion of a cylinder.

14. The vacuum device of claim 1, wherein said contour surface has substantially the shape of a portion of a plane.

15. The vacuum device of claim 1, wherein said fluid impermeable cover is extensible in a direction normal to said contour surface.

16. The vacuum device of claim 1, wherein a set of small traction bumps are located on said contour surface.

17. The vacuum device of claim 1, further comprising an inner perimeter bounding said contour surface such that said contour surface lies between said inner perimeter and said outer perimeter.

* * * * *